United States Patent
Mayfield

(10) Patent No.: US 10,046,840 B2
(45) Date of Patent: Aug. 14, 2018

(54) UNDERWATER OXYGEN BAR

(71) Applicant: Sub Sea Systems, Diamond Springs, CA (US)

(72) Inventor: Jim Mayfield, Diamond Springs, CA (US)

( * ) Notice: Subject to any disclaimer, the term of this patent is extended or adjusted under 35 U.S.C. 154(b) by 0 days.

(21) Appl. No.: 14/198,570

(22) Filed: Mar. 5, 2014

(65) Prior Publication Data
US 2015/0252548 A1   Sep. 10, 2015

(51) Int. Cl.
| | | |
|---|---|---|
| *B63C 11/22* | (2006.01) | |
| *B63C 11/20* | (2006.01) | |
| *A61M 16/12* | (2006.01) | |
| *A61M 16/10* | (2006.01) | |

(52) U.S. Cl.
CPC ............. *B63C 11/20* (2013.01); *A61M 16/12* (2013.01); *B63C 11/22* (2013.01); *A61M 16/1045* (2013.01); *A61M 2202/0208* (2013.01)

(58) Field of Classification Search
CPC ...................................................... B63C 11/20
See application file for complete search history.

(56) References Cited

U.S. PATENT DOCUMENTS

| | | | | |
|---|---|---|---|---|
| 3,515,133 | A * | 6/1970 | Parker ...................... | 128/201.27 |
| 4,905,326 | A * | 3/1990 | Nakamura et al. .............. | 4/488 |
| 6,293,733 | B1 * | 9/2001 | Tezuka .......................... | 405/185 |
| 6,536,431 | B1 * | 3/2003 | Simler ..................... | 128/205.12 |
| 2004/0086838 | A1 * | 5/2004 | Dinis ........................... | 434/247 |
| 2007/0039617 | A1 * | 2/2007 | Buhlmann et al. ...... | 128/201.28 |
| 2008/0004677 | A1 * | 1/2008 | Gay ............................... | 607/85 |

OTHER PUBLICATIONS

Rubber Duckie Designs Nitrox Controller,http://www.rubberduckiedesigns.com/NitroxController.htm, accessed Jan. 24, 2015.*

* cited by examiner

*Primary Examiner* — John J Kreck

(57) ABSTRACT

Described is an underwater oxygen bar. The underwater oxygen bar provides a new recreational experience that unites the unique aquatic experience of being in an underwater environment with the benefits and appeal of an oxygen bar. More specifically, an underwater oxygen bar is provided in which patrons may descend into a water tank wearing a breathing apparatus. Once submerged, the patrons can move about the water tank and interact with an underwater appliance that provides a coupling to a source of an oxygen concentration. Customers can enhance their oxygen experience by using various flavored scents (including, for example, aromatherapy scents) to be added to the oxygen, such as lavender or mint.

15 Claims, 5 Drawing Sheets

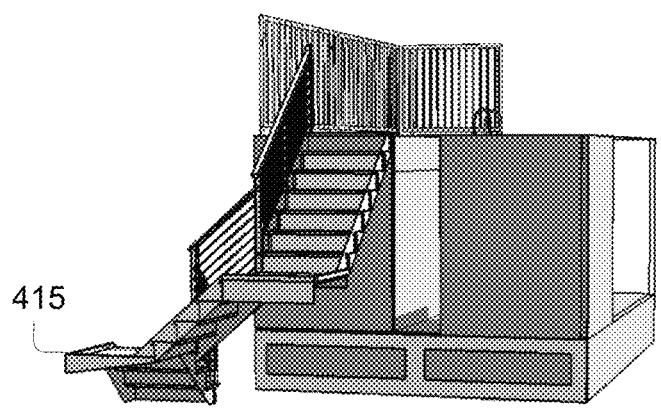
Fig. 4
Fig. 5
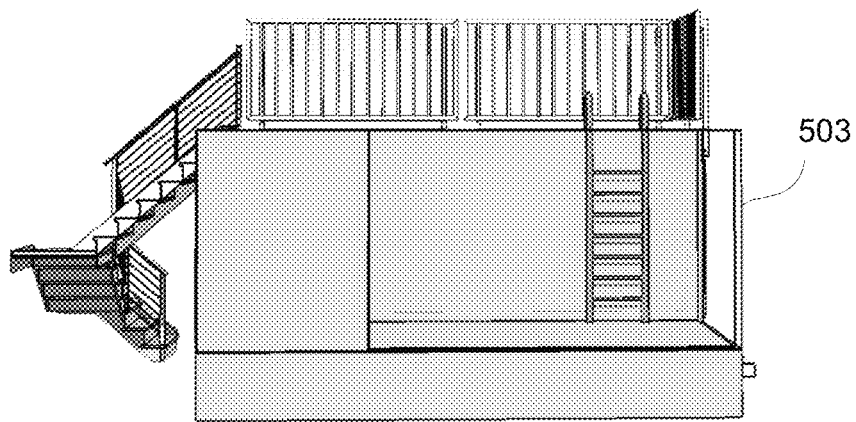

UNDERWATER OXYGEN BAR

TECHNICAL FIELD

The present invention relates to the field of recreational services, and more specifically to the field of aquatic recreational services.

SUMMARY OF THE INVENTION WITH BACKGROUND INFORMATION

Oxygen bars are a growing novelty in many areas of the world. An oxygen bar is, typically, a conventional public meeting place at which the proprietors offer their patrons oxygen to breath.

Oxygen bar guests typically pay a nominal fee to inhale an increased percentage of oxygen compared to the normal atmospheric content of roughly 21% oxygen. This oxygen concentration may be produced from the ambient air using most any acceptable mechanism, such as industrial (non-medical) oxygen concentrators. The oxygen concentration in conventional oxygen bars is typically inhaled through a nasal cannula from a few minutes to about 20 minutes.

Consuming a concentration of oxygen is considered by some to have several health benefits, such as strengthening the immune system, enhancing concentration, reducing stress, increasing energy and alertness, lessening the effects of hangovers, headaches, and sinus problems, and generally relaxing the body. It has also been alleged to help with altitude sickness. Although these claims may not have been substantiated through medical testing, inhaling an oxygen concentration has become popular.

Embodiments of the invention provide users a new recreational experience that also incorporates the benefits and appeal of an oxygen bar. More specifically, an underwater oxygen bar assembly is provided in which patrons may descend into a water tank, pool, aquarium, or other aquatic environment wearing a breathing apparatus. Within the submerged environment, patrons can move about the underwater environment and interact with an appliance that provides a coupling to a source of a concentrated supply of oxygen. Customers can enhance their oxygen experience by using scents to be added to the oxygen, such as lavender or mint. Many different implementations of various embodiments are envisioned.

BRIEF DESCRIPTION OF THE DRAWINGS

Embodiments of the invention will be described in conjunction with the accompanying drawings, briefly described here:

FIG. 4 is another perspective view of one embodiment of the underwater oxygen bar assembly in accordance with the teachings of the invention.

FIG. 5 is yet another perspective view of one embodiment of the underwater oxygen bar assembly in accordance with the teachings of the invention.

DETAILED DESCRIPTION OF EMBODIMENTS

Embodiments of the present invention provide an underwater oxygen bar assembly. Briefly stated, the underwater oxygen bar assembly is designed to operate in an aquarium-like structure sufficiently large to safely accommodate a number of people. The underwater oxygen bar assembly includes an appliance at which a plurality of sources of an oxygen concentration are made available. Each oxygen source is attachable to a breathing apparatus. The breathing apparatus is worn by patrons of the oxygen bar. In practice, patrons may don the breathing apparatus upon entering the underwater oxygen bar assembly. Any patron may wander about the oxygen bar freely, and when desired, may attach an oxygen source to that patron's breathing apparatus to enjoy the benefits and novelty of the oxygen concentration.

Figure 1:
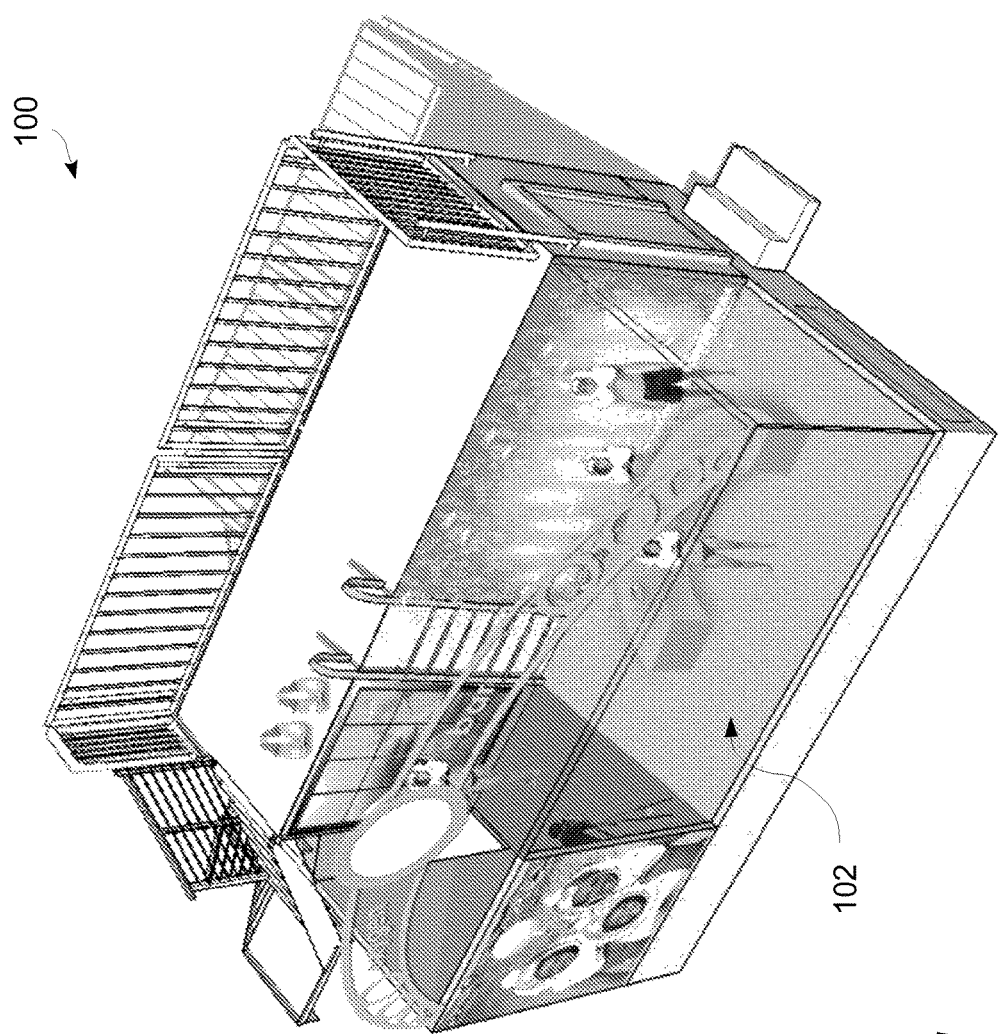
FIG. 1 is a perspective view of one embodiment of an underwater oxygen bar assembly in accordance with the teachings of the invention.

FIG. 1 is a perspective view of one embodiment of an underwater oxygen bar assembly in accordance with the teachings of the invention. FIG. 1 provides a general overview of one way in which the underwater oxygen bar assembly 100 may preferably be implemented. As shown in FIG. 1, the underwater oxygen bar assembly includes a water tank or aquarium environment substantially filled with water (either salt or fresh). Within the tank are several patrons who are enjoying the underwater oxygen bar experience within an underwater oxygen bar 102 of the underwater oxygen bar assembly 100.

Figure 2:
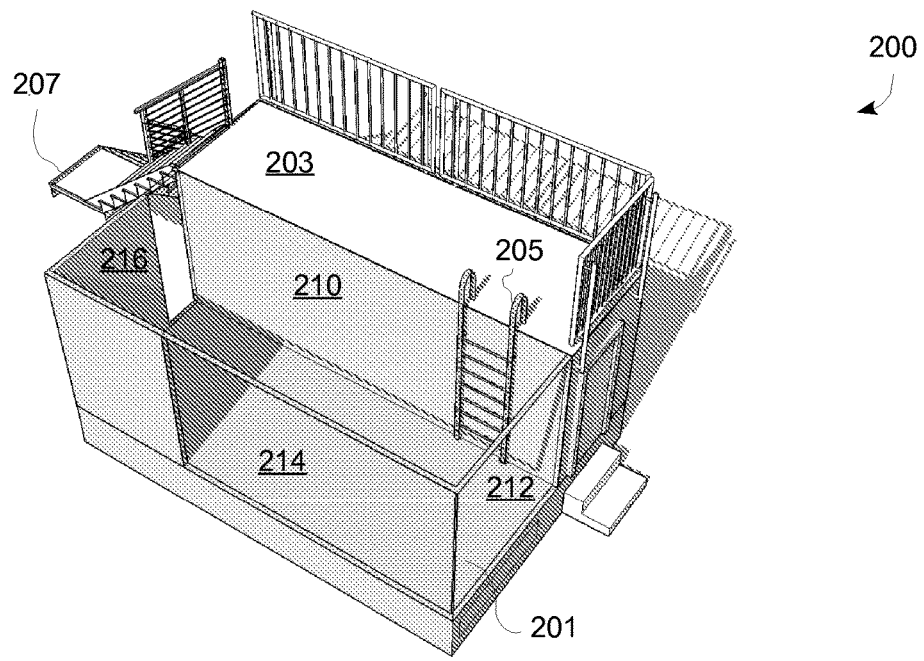
FIG. 2 is another perspective view of an underwater oxygen bar assembly in accordance with the teachings of the invention.

FIG. 2 is another perspective view of an underwater oxygen bar assembly 200 in accordance with the teachings of the invention. As shown in FIG. 2, the underwater oxygen bar assembly 200 includes a water tank 201 that is sufficiently sized to accommodate a number of people. In one particular implementation, the water tank 201 is less than 10,000 gallons and is closed on all sides (e.g., sides 210, 212, 214, and 216) except the top, which is open. The depth of the water tank is sufficient to accommodate patrons who are standing with sufficient water overhead to provide the aquatic experience, yet not so deep that the quantity of water nor is the experience of sufficient duration to suggest or require a special gas or gas mixture. In one preferred embodiment, the water tank 201 is no greater than one atmosphere deep (roughly 33 feet). At the top of the water tank 201 extending from one side (e.g., side 210) is a platform 203 with a ladder 205 that extends downward into the water tank 201. At one end of the platform 203 is a stairway 207 leading from the lower portion of the underwater oxygen bar assembly 200 up to the platform 203.

In this particular implementation, the water tank 201 has sides (e.g., sides 212, 214, and 216) that are substantially transparent. In other implementations, fewer than all the sides may be substantially transparent, or one or more of the sides may be fully or partially opaque. The transparency characteristic promotes the recreational experience by enabling the patrons of the underwater oxygen bar to view their surroundings while being submerged. Viewers outside of the aquarium can also view the activity, and possibly be motivated to participate. Furthermore, the transparency characteristic provides a supplementary mechanism to monitor the safety of the patrons from outside the tank (in addition to the safety staff inside the tank with the guests).

Figure 6:
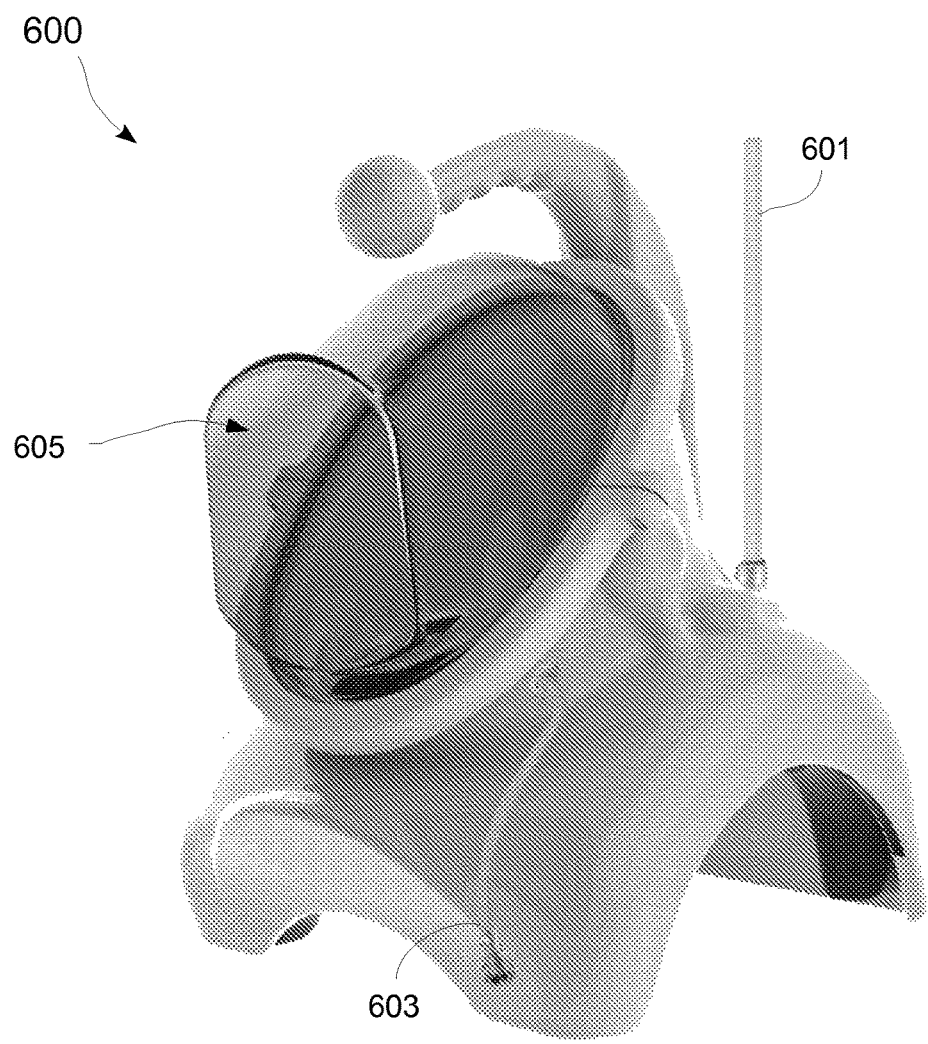
FIGS. 6-8 are illustrations of a preferred breathing apparatus that may be used in various implementations of the invention.
Figure 7:
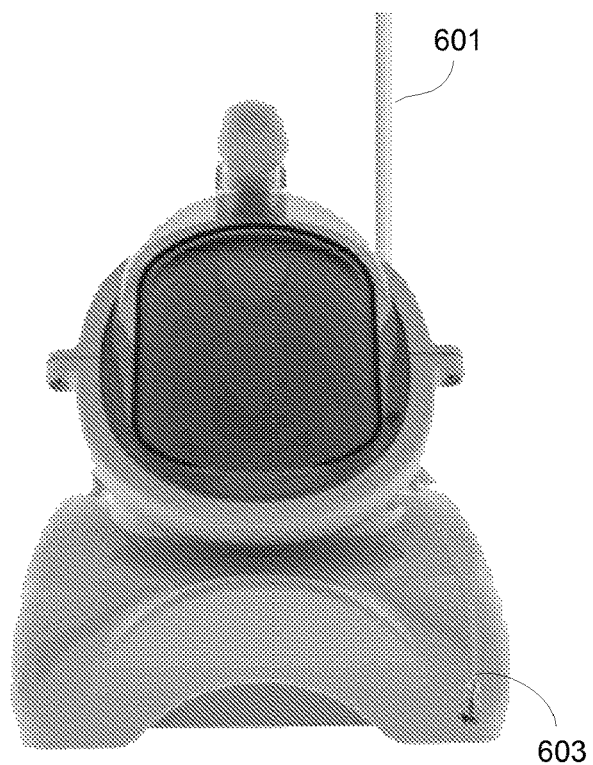
Figure 8:
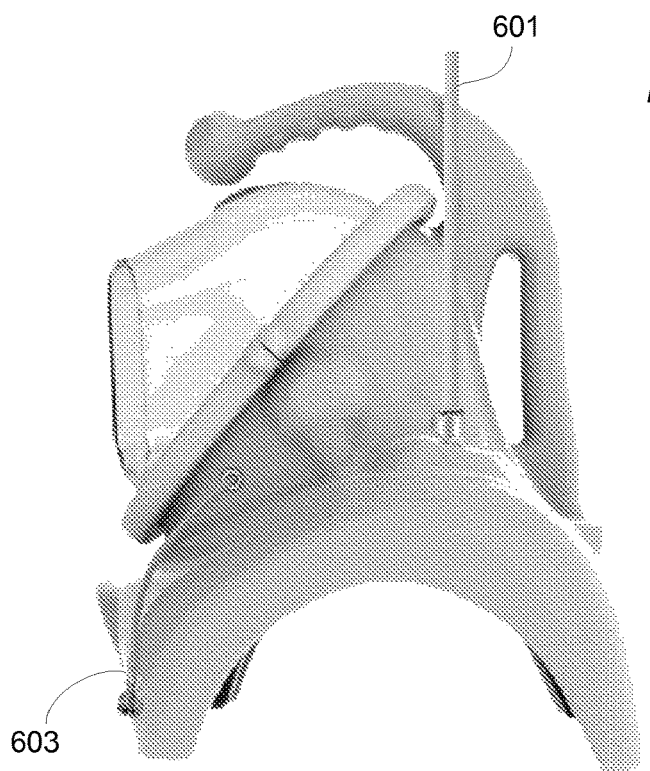

When in use, patrons of the underwater oxygen bar typically arrive to the platform 203 via the stairway 207, at which point the patrons would don a breathing apparatus (shown in FIGS. 6-8), perhaps while descending ladder 205, to enable breathing underwater. One example of a preferred breathing apparatus is a diving helmet as shown in FIGS. 6-8 and described below. Generally stated, the breathing apparatus may be any device or system that enables its wearer to receive and breathe compressed air underwater. At a minimum, the breathing apparatus provides a source of breathable air to its wearer. In addition, the breathing apparatus includes a mechanism for introducing a concentrated oxygen source, or that oxygen source may be delivered through the main air breathing source. Although the preferred embodiments of the invention employ a diving helmet, it should be understood that other breathing apparatuses may be used without deviating from the spirit and scope of the invention.

Once outfitted with the breathing apparatus, the patron submerges into the water tank 201. The patron may be outfitted with sufficient ballast to overcome the natural buoyancy of a person. In the preferred implementation, the breathing apparatus is a diving helmet which is of sufficient weight to provide adequate ballast for a typical person to descend to the bottom of the tank while remaining negatively buoyant. In this manner, the patron experiences a sensation similar to being in a conventional (non-underwater) bar at which the patrons walk freely about the establishment.

The water tank 201 includes an underwater oxygen bar (see underwater oxygen bar 102 in FIG. 1) at which is made available a number of oxygen sources. The oxygen sources provide a source of concentrated oxygen at some level greater than the ambient level. For example, the oxygen sources may provide air that includes oxygen in a concentration of roughly 25%, 30%, 45%, or more (up to 95%). Although less preferred, even substantially pure oxygen may be provided at each of the one or more oxygen sources.

In this particular implementation, the oxygen sources take the form of a detachable hose coupled at one end to a common source of an oxygen concentration, such as provided from an oxygen concentrator. The other end of the oxygen source includes a detachable coupling that mates to a pig tail coupling on a breathing apparatus worn by a patron. The oxygen flows freely into the contained environment of the breathing apparatus worn by the patron, eliminating the need for mechanisms (used to direct the flow of oxygen) stuck into the noses or mouths of the guests.

In another improvement, the oxygen sources may also provide an ability to introduce an aroma or fragrance into the oxygen source. For example, in one implementation, an aroma diffuser is used to inject a scent into the oxygen source for the purpose of aromatherapy or simply the pleasing experience of breathing scented air. Any type of aroma diffuser could be used, such as cold air diffusers, evaporative diffusers, ultrasonic diffusers, humidifiers, vaporizers, or even heated diffusers. These are but a few examples.

Figure 3:
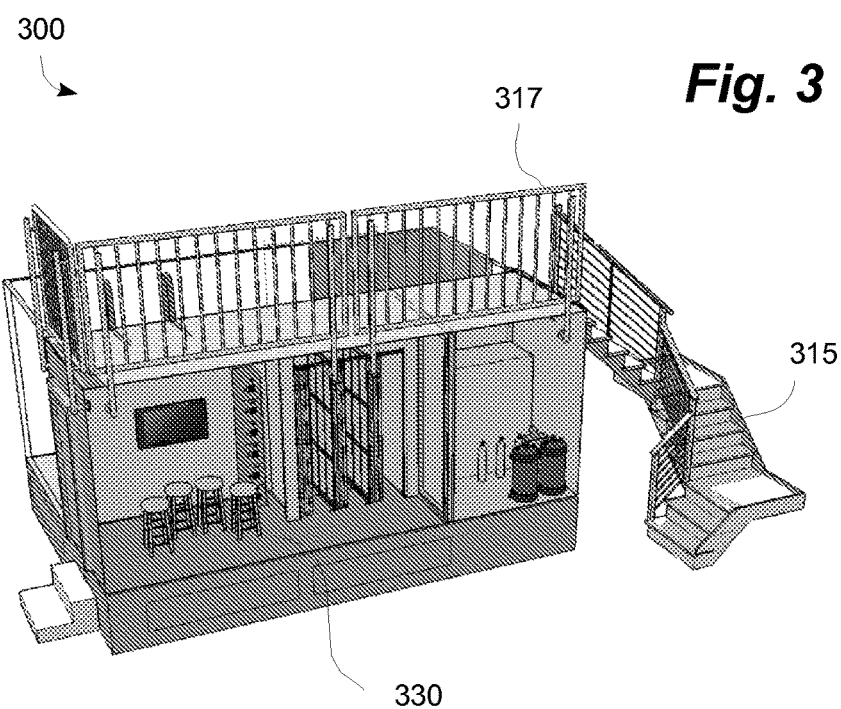
FIG. 3 is a rear view of one particular embodiment of an underwater oxygen bar assembly in accordance with the teachings of the invention.

FIG. 3 is a rear view of one particular embodiment of an underwater oxygen bar assembly 300 in accordance with the teachings of the invention. Visible in the rear view is a generally enclosed area behind the water tank in which are located a source mechanism for providing breathing air (the "breathing source") and a source mechanism for providing an oxygen concentration (the "oxygen source"). In the preferred embodiment, breathing air is provided using a mechanical system for producing compressed air or a vessel containing a source of compressed air gas, and the oxygen concentration is provided using an oxygen generator or a vessel containing a source of compressed oxygen gas. However, it should be understood that in alternative embodiments, the oxygen concentration and the breathing air could be combined into a single source, although it is generally disfavored to provide a controlled oxygen concentration to patrons within the same air breathing source for any extended length of time.

Also visible in the rear view is a storage area 330 in which may be stowed various components of the underwater oxygen bar assembly 300 when not in use, such as during transit. For instance, the stairway 315, the ladder 205 (shown in FIG. 2), and the platform handrails 317 may be detached from the underwater oxygen bar assembly 300 when it is not being used for patrons. Those components may then be stowed away within the storage area 330 for safe keeping. When deployed and the underwater oxygen bar is in its working configuration, the storage area 330 can be used as a work area or break area for people. Although the inside of the storage area 330 of the underwater oxygen bar assembly 300 is visible in the rear view of FIG. 3, it should be appreciated that FIG. 3 presents a cutaway view of the rear of the underwater oxygen bar assembly 300, and in practice the rear would likely, but not necessarily, be enclosed.

In the preferred embodiment, the underwater oxygen bar assembly and its various components are designed and sized such that when in its stowed configuration, the outside dimensions of the resultant stowed configuration approximate the size of a typical shipping container. In this way, the underwater oxygen bar assembly can be disassembled into its stowed configuration and relatively easily shipped to distant destinations using standard shipping protocols. In other alternatives, the ability to transport the structure is less desirable or not necessary (such as fixed-location implementations), so the size of the structure would not be based on the size of a typical shipping container.

FIG. 4 is another perspective view of one embodiment of the underwater oxygen bar assembly in accordance with the teachings of the invention. FIG. 4 shows in greater detail the stairway 415 that leads from generally the ground up to the platform. In use, patrons who desire to experience the underwater oxygen bar mount the stairway to the platform, where they would enter the water tank from above the water tank using the ladder. In other implementations, the water tank could be an in-ground facility or perhaps an aquarium, in which case the stairway could be unnecessary.

FIG. 5 is yet another perspective view of one embodiment of the underwater oxygen bar assembly in accordance with the teachings of the invention. Shown in FIG. 5 is a view of the underwater oxygen bar assembly as may be viewed from so-called street level or as passers-by may encounter the facility. As shown in FIG. 5, a person walking by the facility has a view into the water tank 503 through the transparent walls. In that way, the underwater oxygen bar assembly provides substantial promotional benefits and curb appeal in areas having a nautical or aquatic theme, such as a beach area, boardwalk, water park, aquarium, or resort destination.

FIGS. 6-8 are illustrations of a preferred breathing apparatus that may be used in various implementations of the invention. As shown in FIG. 6, the preferred breathing apparatus is a diving helmet 600 having one or two couplings for air and an oxygen concentration. In the preferred implementation, a first connector 601 provides ordinary breathable air such as may be provided with a typical underwater breathing apparatus that uses a remote compressed air source. Alternatively, the first connector 601 could be an attachment for coupling to a compressed air canister or diving cylinder as may be used with scuba equipment.

The second connector 603 may be a pigtail connector to which may be mated an oxygen source that provides an oxygen concentration. In this implementation, the diving helmet 600 introduces both the air from the first connector 601 and the oxygen concentration from the second connector 603 into the breathing space 605 within the diving helmet 600. In addition, any scent or other additive may be introduced with the oxygen concentration through the second connector 603 and/or may be introduced through the first connector.

The diving helmet 600 is worn over the head, resting on the shoulders of the patron so as to provide a breathing environment. Through the first and second connectors, a mixture of air, an oxygen concentration, and (optionally) scents may be introduced into the breathing environment. Although other breathing apparatuses may be used, the diving helmet is preferred because it simplifies the underwater oxygen bar experience. For instance, a diving helmet is simpler and easier to place over one's head (resting on the shoulders), and reduces the anxiety that frequently occurs when people who are unfamiliar with scuba diving are first introduced to breathing underwater.

Still further, the diving helmet 600 does not obstruct the face of the wearer, which enables even more opportunities. For example, in addition to (or as a possible alternative to) a breathable oxygen concentration introduced through the second connector, the wearer could perhaps be provided with a drinking tube that extends from a sealed beverage. In this way, the underwater oxygen bar could even serve beverages in the nature of a typical bar or pub. In still another enhancement, the diving helmet could include a wireless short-range communication system that enables multiple patrons to speak to each other, thus further enhancing the enjoyment of the experience.

Returning again to FIG. 1, the underwater oxygen bar experience is generally described as providing a new aquatic recreational experience. Patrons of the underwater oxygen bar would mount the stairway (if the water tank is above ground) to the platform where they would don a breathing apparatus, such as the preferred diving helmet. The patron would descend into the water tank using the ladder, if necessary. In the preferred implementation, the breathing apparatus would be lowered onto the shoulders of the patron as he or she entered the water because of the weight of the diving helmet, which provides the ballast to enable the patron to descend to the bottom of the water tank or aquarium structure. In alternative embodiments, the patrons could wear scuba gear, which would eliminate any need for the ladder.

Once fully submerged, the patron descends to the bottom of the water tank and can move about the bottom. Of course, the patrons' movement through the water density is not identical to movement on dry land, which is the purpose of the experience. When desired, the patron can move to a location proximate to the underwater oxygen bar at the bottom of the water tank or aquarium environment. Perhaps with the assistance of a "bartender," the patron connects the breathing apparatus to an oxygen source exposed at the underwater oxygen bar. In this way, the patrons can each enjoy their concentrated oxygen experience while submerged. And if the breathing apparatus is outfitted with a wireless intercom system, they can communicate with each other.

It is envisioned that the proprietor of the underwater oxygen bar will make use of safety divers within the water tank while any patrons are submerged. Those safety divers could also serve additional, ancillary roles as a bartender (as discussed above) and even, perhaps, a photographer to capture pictures of the patrons during their experience. Many different alternatives are possible.

Although the invention has been described in the context of certain preferred embodiments, those skilled in the art will understand that these embodiments are merely illustrative and that many alternative embodiments are taught and suggested by this disclosure. Accordingly, the invention is not limited to these specific preferred embodiments, and rather, the invention is limited only by the following claims, which alone define the full scope of the invention.

The invention claimed is:

1. A recreational facility, comprising:
   an underwater oxygen bar assembly, including
   a source of compressed gas containing a first gas, the first gas being substantially ambient air;
   at least one source for a second gas, the at least one source providing the second gas at a respective oxygen concentration greater than substantially ambient air;
   a water tank sized sufficiently to completely submerge a plurality of people, the water tank further including a platform towards a top of the water tank, wherein the platform is configured to permit the plurality of people to enter the water tank at the top of the water tank, wherein the water tank is configured to be filled with water at a depth to submerge the number of people while the people are in a substantially upright position; and
   a breathing apparatus for each of the plurality people, each respective
   breathing apparatus being configured to be worn by each of the people while completely submerged in the water tank and configured to receive the first gas and the second gas such that the breathing apparatus enables breathing substantially ambient air if exposed to only the first gas and, when selected by at least one of the plurality of people, enables additionally, for the at least one of the plurality of people, breathing the respective oxygen concentration associated with the second gas while the at least one of the plurality of people is completely submerged in the water tank.

2. The recreational facility recited in claim 1, further comprising a scent source operative to introduce a scent into the second gas.

3. The recreational facility recited in claim 1, wherein the breathing apparatus comprises a diving helmet.

4. The recreational facility recited in claim 3, wherein the diving helmet includes at least one coupling for receiving at least the first gas.

5. The recreational facility recited in claim 4, wherein the at least one coupling is further operative to receive the second gas.

6. The recreational facility recited in claim 4, wherein the diving helmet includes a second coupling for receiving the second gas separate from the first gas.

7. The recreational facility recited in claim 3, wherein the diving helmet includes at least two couplings, one coupling for receiving the first gas and another coupling for receiving the second gas.

8. The recreational facility recited in claim 1, wherein the breathing apparatus includes a sufficient weight to provide adequate ballast for the person wearing the breathing apparatus to descend to the bottom of the water tank while remaining negatively buoyant.

9. A method of recreation, comprising:
providing a water tank sized sufficiently to accommodate a plurality of people, the water tank being no greater than one atmosphere deep;
providing a first gas, the first gas being substantially ambient air for breathing;
providing a second gas, the second gas being a concentration of oxygen at a level significantly above the mix of substantially ambient air;
filling the water tank with water at a depth to submerge the plurality of people while the people are in a substantially upright position; and
making the water tank available to the number of people who each enter the water tank at a top portion of the water tank via a platform wearing a breathing apparatus, the breathing apparatus configured to be worn by each of the people while completely submerged in the water tank, the breathing apparatus operative to receive the first gas and the second gas and to deliver either the first gas, or a combination of the first gas and the second gas upon selection while the breathing apparatus is submerged and worn by each of the people.

10. The method recited in claim 9, further comprising providing a scent source operative to introduce a scent into the breathing apparatus.

11. The method recited in claim 9, wherein the breathing apparatus comprises a diving helmet.

12. The method recited in claim 11, wherein the diving helmet includes at least one coupling for receiving the first gas, the second gas, or a combination of the first gas and the second gas.

13. The method recited in claim 11, wherein the diving helmet includes at least two couplings for receiving the first gas and the second gas.

14. The method recited in claim 9, wherein the breathing apparatus includes a sufficient weight to provide adequate ballast for the patron wearing the breathing apparatus to descend to the bottom of the water tank while remaining negatively buoyant.

15. The method recited in claim 9, further comprising providing a scent to the breathing apparatus.

* * * * *